United States Patent [19]

Luteijn et al.

[11] Patent Number: 4,842,718

[45] Date of Patent: Jun. 27, 1989

[54] PROCESS FOR RECOVERY OF HYDROCARBONS FROM A FLUID FEED

[75] Inventors: Cornelis P. Luteijn; Michel Muylle; Carolus T. Sanders, all of The Hague, Netherlands

[73] Assignee: Shell Oil Company, Houston, Tex.

[21] Appl. No.: 109,893

[22] Filed: Oct. 19, 1987

[30] Foreign Application Priority Data

Sep. 30, 1986 [GB] United Kingdom ............... 8623431

[51] Int. Cl.$^4$ .............................................. B01D 59/12
[52] U.S. Cl. ................................... 208/308; 208/103; 585/818; 55/158; 55/16
[58] Field of Search .................... 55/158, 16; 208/308, 208/100, 102, 103; 585/818

[56] References Cited

U.S. PATENT DOCUMENTS 3,250,080  5/1966  Garwin ................................. 55/16
3,718,575  2/1973  Watkins .............................. 208/103
4,204,338  4/1981  Null ..................................... 55/158
4,732,583  3/1988  Delong et al. ...................... 55/158

Primary Examiner—Glenn Caldarola
Attorney, Agent, or Firm—Ronald R. Reper

[57] ABSTRACT

A process for recovery of hydrocarbon ($C_2^+$) containing at least two carbon atoms per molecule (e.g. LPG) from a fluid feed containing $C_2^+$ hydrocarbons and components having at most one carbon atom per molecule (e.g. refinery gas) comprising the following steps:

(i) contacting the fluid feed with one side of at least one membrane which is substantially non-permeable for $C_2^{30}$ hydrocarbons and removing a first fluid (permeate) containing a substantial amount of components having at most one carbon atom per molecule from the other side of the membrane(s), and (ii) fractionating fluid (retentate) obtained from the one side of the membrane(s) into at least a product containing $C_2^{30}$ hydrocarbons and a gaseous product.

7 Claims, No Drawings

PROCESS FOR RECOVERY OF HYDROCARBONS FROM A FLUID FEED

BACKGROUND OF THE INVENTION

The invention relates to a process for recovery of hydrocarbons from a fluid feed.

It is known to fractionate fluid feed streams containing hydrocarbons having at least two carbon atoms per molecule ($C_2$) in addition to components having at most one carbon atom per molecule which components (e.g. hydrogen, methane, carbon oxides and/or nitrogen) have a lower boiling point than the $C_2$ hydrocarbons, by means of one or more processes such as chilling, cryogenic separation, absorption and compression. However, the energy requirements of such processes are relatively high and whereas valuable components such as hydrogen generally remain in the low boiling (fuel) gas stream thus separated from the $C_2$ hydrocarbons.

It is furthermore known to separate a particular component such as hydrogen or carbon dioxide selectively from a gaseous feed mixture containing other components (e.g. methane and other hydrocarbons or nitrogen) by contacting said feed mixture with one side of a membrane and removing the component which selectively permeates through the membrane from the other side thereof, before subjecting the non-permeated feed fraction to a cryogenic separation treatment.

A major disadvantage of such processes is, however, that substantial volumes of components having a relatively low boiling point are passed through a (e.g. cryogenic) fractionation unit which accordingly has to have a relatively high capacity for a given quantity of the initial feed mixture which is contacted with the membrane.

It is an object of the present invention to provide an efficient process for the recovery of $c_2$ hydrocarbons from a fluid feed also containing components having at most one carbon atom per molecule without incurring the aforementioned disadvantages.

It has now been found that by using a membrane which is substantially impermeable to $C_2$ hydrocarbons in a first separation step, and fractionating the retentate fluid obtained therefrom in a second separation step, a high separation efficiency can be attained with substantial savings in fractionation equipment, compared with a fractionation such as such.

SUMMARY OF THE INVENTION

The invention therefore relates to a process for recovery of hydrocarbons ($C_2$) having at least two carbon atoms per molecule from a fluid feed containing $C_2$ hydrocarbons and components normally boiling at temperatures lower than $C_2$ hydrocarbons and having at most one carbon atom per molecule which comprises the following steps:
(i) contacting the fluid feed with one side of at least one membrane which is substantially non-permeable for $C_2$ hydrocarbons and removing a first fluid (permeate) containing a substantial amount of components having at most one carbon atom per molecule from the other side of the membrane(s), and
(ii) fractionating fluid (retentate) obtained from the one side of the membrane(s) into at least a product containing $C_2$ hydrocarbons and a gaseous product.

DESCRIPTION OF PREFERRED EMBODIMENTS

A wide variety of fluid feeds can be separated into the desired fractions by means of the present process which is particularly suited for gaseous feeds such as platformer off gas and/or refinery fuel gas from which not only $C_2$ hydrocarbons can be recovered but also hydrogen which is highly desirable in modern refineries employing hydroconversion units.

Besides methane and hydrogen, the first fluid obtained in step (i) may optionally contain water vapor which is advantageous when a cryogenic separation is applied in step (ii) due to the possibility to apply less drying, or even no drying at all, to the retentate fluid from the membrane separation step before passing said fluid to the cryogenic zone. Normally, drying (e.g. using e.g. a zeolitic molecular sieve material which selectively adsorbs water) would be necessary in a conventional setup in order to avoid freezing-up of lines in the cryogenic unit.

Preferably, the first fluid obtained in step (i) contains more than 80% and in particular more than 90%, by weight of components having at most one carbon atom per molecule, calculated on basis of the total amount of first fluid.

When the fluid feed which is used in the process according to the invention contains methane in an amount which is undesired in the retentate fluid obtained from step (i), e.g. more than 10 mol% and in particular more than 30 mol% of methane, based on the fluid feed, the membrane applied in step (i) is preferably substantially permeable for methane in order to remove methane from the retentate fluid which is further processed downstream in one or more fractionation units; these units can consequently be downsized, compared with the use of membranes which are non-permeable for methane, resulting in substantial savings in capital outlay and operating costs of the fractionation units.

In a gas permeation process, in which a difference in pressure is maintained between both sides of the membrane as the driving force, various types of membrane units may be applied such as a flat sheet or a tubular membrane uit. Flat membranes are less attractive in case the differential pressure relatively high, acquiring small pores in order to have sufficient strength to withstand the applied pressure differences, and consequently the permeate flux through flat membranes would be relatively low in this case. Moreover, such configurations require a relatively large amount of volume because their packing density ($m^2$ membrane/$m^3$ apparatus) is low. Preference is given to the application of spirally wound- and/or hollow fiber membranes which have a high packing density and can withstand a relatively high prssure difference between both sides of the membrane for a given wall thickness.

The pressure difference applied between the one side of the membrane contacted with the fluid feed and the other (permeate) side is preferably from 2–200 bar, and most preferably from 10–100 bar.

The temperature at which the present process is carried out may vary within a wide range and is not critical as long as the applied membranes can withstand the operating conditions. A fluid feed temperature from $-40°$ C. to $+400°$ C. is suitable is most cases, whereas a temperature from $-20°$ C. to $+200°$ C. particularly $0°$ C. to $70°$ C. is preferred.

Various membrane materials can be applied in step (i) of the process according to the invention, provided that these materials are substantially non-permeable for $C_2$ hydrocarbons. Suitable materials include modified cellulose compounds such as cellulose acetate, polyamide, polyimide, polyalkylenes (in particular polymethylpentene), polysulphone and silicon-containing polymers.

It has been found that membranes containing a layer of a silicone polymer as described hereinafter are particularly suitable as selective membranes for application in the process according to the invention. Said silicone polymer comprises units according to the general formula:

wherein $R_1$ and $R_2$ represent moieties independently chosen from the group consisting of hydrogen, halogen, alkyl-, aryl-and aralkyl-moieties, and halogen-substituted alkyl-, aryl- and aralkyl-moieties; the carbon-containing moieties may have 1–10 carbon atoms per moiety. Preferably, $R_1$ and $R_2$ represent the same or different (halogensubstituted) alkyl moieties.

The membrane suitably comprises the silicone compound as described hereinbefore in the form of a cross-linked polymer; however, a copolymer of said silicone compound and an elastomeric prepolymer may be used instead.

Various elastomers such as (synthetic) rubbers, polystyrene, polybutadiene or copolymers of styrene and butadiene can also be applied as selective membrane layers per se in the process according to the invention.

The selective membrane layer applied in the present process is suitably substantially non-porous (dense) in order to avoid permeation of substantial amounts of $C_2$ hydrocarbons through said layer; said membrane layer or hollow fiber membrane preferably has a thickness from 0.1–100 $\mu$m, and most preferably from 1–10 $\mu$m, in order to attain relatively high permeate fluxes therethrough.

The use of reinforcing filler in the membrane layer is preferably avoided because of a possible negative influence thereof on the permeability and/or pressure resistance of said membrane layer. A membrane with excellent strength for the present purpose can be obtained by supporting the silicone layer by means of a porous support which may contain a layer of any suitable material, such as cloth, wire net or glass fibers, in case flat- or spiral wound membranes are applied. A porous polypropylene support layer is preferred in case a silicone polymer is applied as non-porous membrane layer in view of the adhesive bond which can be attained between these two layers; such a support layer suitably has a thickness from 10–500 $\mu$m, and preferably from 15–100 $\mu$m. In some cases it may be advantageous to apply at least one extra layer between a dense, selective layer and a porous support; this intermediate layer is suitably a dense (i.e. non-porous), but highly permeable layer with good bonding capacity for both the selective layer and the support.

Step (i) of the present process can be applied in single- or multi-step operation.

The retentate fluid is generally obtained from step (i) at a pressure which is substantially equal to the pressure at which the fluid feed is introduced into the membrane unit employed in step (i). Consequently, it is possible to separate off at least part of the desired produce containing $C_2$ hydrocarbons by expanding at least part of the retentate fluid to a lower pressure while performing work in a turbo expander and thus cooling the retentate fluid to obtain condensed liquids. The condensed liquids may subsequently be separated by means of low temperature distillation into e.g. a fuel gas, ethane and/or ethylene (and propylene) and a $C_3$ hydrocarbon fraction (containing molecules) having at least three carbon atoms; e.g. liquified petroleum gas.

Alternatively, the retentate fluid obtained from step (i) can be subjected to an absorption treatment e.g. using (liquid) butane or a butane-containing stream as absorbent, thus obtaining a fuel gas from the absorption unit in addition to a $C_2$ fraction containing the butane absorbent. Said $C_2$ fraction can be separated further in e.g. a fractionator to remove ethane and/or ethylene therefrom.

Furthermore, it is envisaged to carry out step (ii) of the process according to the invention by moderately cooling the retentate fluid obtained from step (i) (e.g. to a temperature between 5° C. and 15° C.) and subsequently flashing the chilled fluid to separate fuel gas (e.g. a gas containing molecules having at most one carbon atom) from a product containing $C_2$ and preferably only $C_3$ hydrocarbons.

Moreover, retentate fluid can be separated into fuel gas and a $C_2$ product by means of a so called recontacting operation in which the retentate fluid is separated (e.g. at a temperature from $+40°$ C. to $-70°$ C. and a pressure from 2 to 40 bar abs.) into a liquid-and a gaseous fraction (after compression- and/or cooling stages). At least part of the gaseous fraction is compressed and subsequently recontacted with at least part of the liquid fraction. Subsequently, the recontacted mixture is separated in a recontacting zone into the desired liquid and gaseous product fractions.

The invention further relates to hydrocarbons whenever obtained by a process as described hereinbefore.

The following Example illustrates the invention.

EXAMPLE

A fluid feed mixture containing 37 parts by volume (V) of $C_2$ hydrocarbons per 100 parts (V) of feed (i.e. 23 parts (V) of $C_3$ hydrocarbons and 14 parts (V) of components having two carbon atoms per molecule) and 63 parts (V) of components having at most one carbon atom per molecule is contacted at a pressure of 35 bar abs. and a temperature of 70° C. with a polyimide hollow fiber membrane. The retentate fluid thus obtained at a pressure of 35 bar abs. has a volume of 50 parts, on basis of 100 parts (V) of feed, whereas the dewpoint thereof is increased by 26° C.; 90% by weight of the $C_2$ hydrocarbon fraction, calculated on basis of the $C_2$ hydrocarbons in the fluid feed mixture, is present in the retentate fluid. The permeate is obtained at a pressure of 1.5 bar abs. and substantially contains hydrogen, water and methane.

The retentate fluid is further separated by means of fractionation into $C_3$ fraction and fuel gas.

We claim:

1. Process for recovery of hydrocarbons ($C_2$) having at least two carbon atoms per molecule from a fluid feed containing $C_2$ hydrocarbons and components normally boiling at temperatures lower than $C_2$ hydrocarbon and having at most one carbon atom per molecule which comprises the following steps:

(i) contacting the fluid feed with one side of at least one membrane which is substantially permeable for methane and substantially non-permeable for $C_2$ hydrocarbons to afford permeate fluid containing a substantial amount of components having at most one carbon atom per molecule and a retentate fluid having a $C_2$ hydrocarbon content higher than said feed to the membrane(s), and (ii) fractionating by fractionation distillation said retentate fluid into at least a product containing $C_2$ hydrocarbons and a gaseous product.

2. Process according to claim 1 wherein the fluid feed contains at least one of platformer off gas and refinery fuel gas.

3. Process according to claim 1 wherein said contacting is carried out at a pressure differential from 2 to 200 bar between the retentate, —and the permeate—side of the membrane(s).

4. Process according to claim 1 wherein said permeate fluid obtained in step (i) contains hydrogen and optionally water vapor.

5. Process according to claim 1 wherein at least part of the retentate fluid obtained from step (i) is expanded before being fractionated in step (ii).

6. Process according to claim 1 wherein step (ii) is a cryogenic separation.

7. Process according to claim 1 wherein step (ii) includes absorption of $C_2$ hydrocarbons with a butane-containing absorbent.

* * * * *